(12) United States Patent
Fukumoto et al.

(10) Patent No.: US 11,220,649 B2
(45) Date of Patent: Jan. 11, 2022

(54) FLUORINE-CONTAINING ETHER COMPOUND, LUBRICANT FOR MAGNETIC RECORDING MEDIUM, AND MAGNETIC RECORDING MEDIUM

(71) Applicant: SHOWA DENKO K.K., Tokyo (JP)

(72) Inventors: Naoya Fukumoto, Ichihara (JP); Daisuke Yagyu, Ichihara (JP); Yuta Yamaguchi, Kawasaki (JP); Shoko Uetake, Ichihara (JP); Tsuyoshi Kato, Ichihara (JP); Hiroyuki Tomita, Ichihara (JP); Ryuuta Miyasaka, Ichihara (JP); Katsumi Murofushi, Ichihara (JP)

(73) Assignee: SHOWA DENKO K.K., Tokyo (JP)

( * ) Notice: Subject to any disclaimer, the term of this patent is extended or adjusted under 35 U.S.C. 154(b) by 18 days.

(21) Appl. No.: 16/480,464

(22) PCT Filed: Dec. 4, 2017

(86) PCT No.: PCT/JP2017/043451
§ 371 (c)(1),
(2) Date: Jul. 24, 2019

(87) PCT Pub. No.: WO2018/139058
PCT Pub. Date: Aug. 2, 2018

(65) Prior Publication Data
US 2019/0382675 A1    Dec. 19, 2019

(30) Foreign Application Priority Data

Jan. 26, 2017 (JP) .............................. JP2017-012345

(51) Int. Cl.
*C10M 105/54* (2006.01)
*C07C 43/178* (2006.01)
(Continued)

(52) U.S. Cl.
CPC ....... *C10M 105/54* (2013.01); *C07C 43/1786* (2013.01); *C08G 65/331* (2013.01);
(Continued)

(58) Field of Classification Search
CPC .............. C10M 107/38; C10M 105/54; C10M 2213/0606; C10M 2213/06;
(Continued)

(56) References Cited

U.S. PATENT DOCUMENTS 4,526,833 A * 7/1985 Burguette ............ C09D 171/02
428/336
2005/0123855 A1    6/2005 Hegel
(Continued)

FOREIGN PATENT DOCUMENTS

JP    61-126052 A    6/1986
JP    11-071440 A    3/1999
(Continued)

OTHER PUBLICATIONS

International Search Report for PCT/JP2017/043451 dated Feb. 27, 2018 [PCT/ISA/210].
(Continued)

*Primary Examiner* — Vishal V Vasisth
(74) *Attorney, Agent, or Firm* — Sughrue Mion, PLLC

(57) ABSTRACT

A fluorine-containing ether compound represented by Formula (1) is provided;

$$R^1\text{—}R^2\text{—}CH_2\text{—}R^3\text{—}CH_2\text{—}R^4\text{—}R^5 \quad (1)$$

(In Formula (1), $R^1$ and $R^5$ may be the same as or different from each other and each represents an alkenyl group having 2 to 8 carbon atoms or an alkynyl group having 3 to 8 carbon atoms, $R^2$ and $R^4$ may be the same as or different from each other and each represents a divalent linking group having a polar group, and $R^3$ represents a perfluoropolyether chain, (Continued)

with a proviso that $R^1$ and $R^2$ are, and $R^4$ and $R^5$ are divided due to the presence of an atom other than the carbon atom such as an oxygen atom).

8 Claims, 1 Drawing Sheet

(51) Int. Cl.
| | |
|---|---|
| *G11B 5/725* | (2006.01) |
| *C08G 65/331* | (2006.01) |
| *C10M 107/38* | (2006.01) |
| *C10N 20/04* | (2006.01) |
| *C10N 30/06* | (2006.01) |
| *C10N 50/00* | (2006.01) |
| *C10N 40/18* | (2006.01) |

(52) U.S. Cl.
CPC ............ *C10M 107/38* (2013.01); *G11B 5/725* (2013.01); *C10M 2213/06* (2013.01); *C10M 2213/0606* (2013.01); *C10N 2020/04* (2013.01); *C10N 2030/06* (2013.01); *C10N 2040/18* (2013.01); *C10N 2050/023* (2020.05)

(58) Field of Classification Search
CPC ............ C10N 2040/18; C10N 2030/06; C10N 2020/04; C10N 2050/023; C08G 65/331; C07C 43/1786
See application file for complete search history.

(56) References Cited

U.S. PATENT DOCUMENTS

| | | |
|---|---|---|
| 2009/0281250 A1 | 11/2009 | DeSimone et al. |
| 2010/0261039 A1 | 10/2010 | Itoh et al. |
| 2012/0225217 A1 | 9/2012 | Itoh et al. |
| 2013/0209837 A1 | 8/2013 | Sagata et al. |
| 2015/0274960 A1* | 10/2015 | Fukuda .................. C08L 71/02 525/102 |
| 2015/0371672 A1* | 12/2015 | Sagata .................. G11B 5/725 428/833 |
| 2016/0068778 A1 | 3/2016 | Conley et al. |
| 2018/0022851 A1* | 1/2018 | Takao ................ C08G 18/2885 522/39 |

FOREIGN PATENT DOCUMENTS

| | | |
|---|---|---|
| JP | 2866622 B2 | 3/1999 |
| JP | 2000-264883 A | 9/2000 |
| JP | 2001-134924 A | 5/2001 |
| JP | 2001-209924 A | 8/2001 |
| JP | 2002-069037 A | 3/2002 |
| JP | 2004-115640 A | 4/2004 |
| JP | 2006-131874 A | 5/2006 |
| JP | 2010-241831 A | 10/2010 |
| JP | 2012-009090 A | 1/2012 |
| JP | 2013-163667 A | 8/2013 |
| JP | 6122191 B1 | 4/2017 |
| WO | 2009/123043 A1 | 10/2009 |

OTHER PUBLICATIONS

Office Action dated Mar. 11, 2021 from the China National Intellectual Property Administration in CN Application No. 201780070908.1.

* cited by examiner

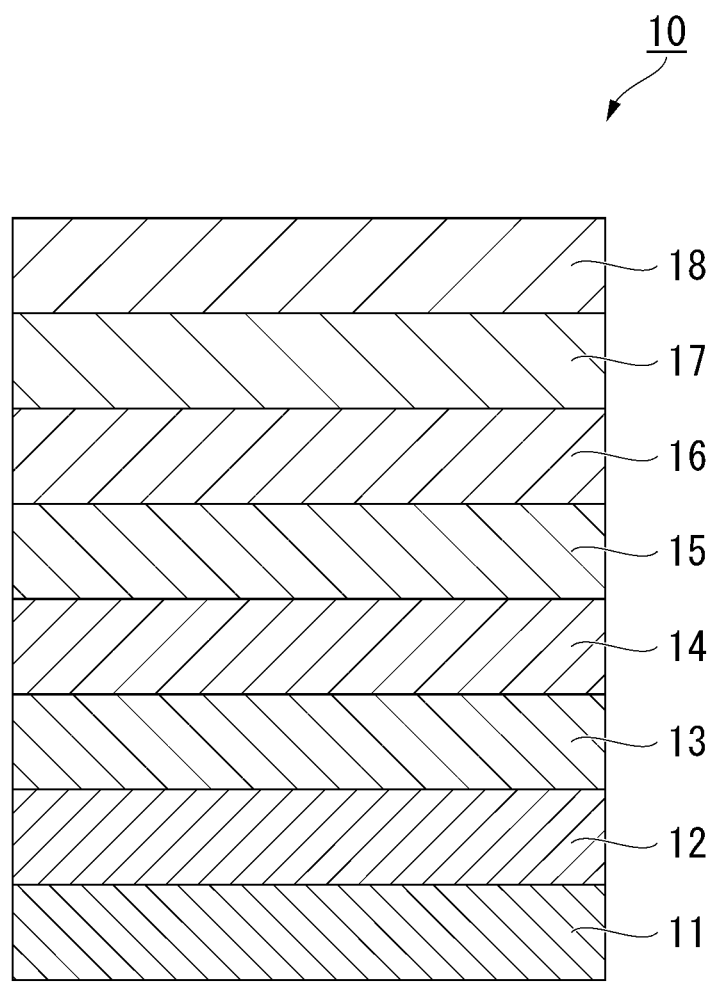

US 11,220,649 B2

FLUORINE-CONTAINING ETHER COMPOUND, LUBRICANT FOR MAGNETIC RECORDING MEDIUM, AND MAGNETIC RECORDING MEDIUM

TECHNICAL FIELD

The present invention relates to a fluorine-containing ether compound suitable for lubricant application in a magnetic recording medium, a lubricant for a magnetic recording medium, and a magnetic recording medium which include the same. This application is a National Stage of International Application No. PCT/JP2017/043451, filed on Dec. 4, 2017, which claims priority from Japanese Patent Application No. 2017-012345, filed on Jan. 26, 2017, the content of which is incorporated herein by reference.

BACKGROUND ART

With the increase in capacity of information processing in recent years, various information recording technologies have been developed. In particular, development of a magnetic recording medium suitable for high recording density is in progress.

A magnetic recording medium generally includes a protective layer and a lubricating layer on a magnetic recording layer formed on a substrate, in order to ensure durability and reliability of the magnetic recording medium. In particular, the lubricating layer provided on an outermost surface is required to have various characteristics such as long-term stability, chemical resistance (preventing contamination with siloxane and the like), and wear resistance.

In response to such a requirement, a perfluoropolyether lubricant including an unsaturated group in a molecule is often used as a lubricant for a magnetic recording medium.

As the perfluoropolyether lubricant, for example, a lubricant including a polymerizable unsaturated group-containing perfluoropolyether compound is known (see, for example, Patent document 1). In the lubricant, when the polymerizable unsaturated group-containing perfluoropolyether compound is polymerized by an active energy ray irradiation treatment, bonding strength between the lubricants increases, and excellent coefficient of static friction and spin-off characteristics are exhibited.

In addition, as the perfluoropolyether lubricant, for example, a lubricant including a photocrosslinkable functional group-containing compound is known (see, for example. Patent document 2). In the lubricant, when the photocrosslinkable functional group-containing compound is crosslinked, the lubricants are bonded to each other and a high bonding rate is exhibited.

In addition, as the perfluoropolyether lubricant, for example, a lubricant including a fluorine-containing compound having an alkenyl group which may have a polar group is known (see, for example, Patent document 3). The lubricant exhibits excellent lubricity coefficient of friction.

CITATION LIST

Patent Documents

Patent document 1: Japanese Unexamined Patent Application, First Publication No. 2001-209924
Patent document 2: Japanese Unexamined Patent Application, First Publication No. 2001-134924
Patent document 3: Japanese Patent No. 2866622

SUMMARY OF INVENTION

Technical Problem

With the rapid improvement in information recording density of a magnetic recording medium in recent years, a reduction in the magnetic spacing between a magnetic head and a recording layer of the magnetic recording medium has been required. Therefore, further thinning of the lubricating layer present between the magnetic head and the recording layer of the magnetic recording medium has been required. The lubricant used for the lubricating layer forming an outermost surface of the magnetic recording medium has a significant influence on the durability of the magnetic recording medium. However, for example, even if the lubricating layer is thinned, reliability such as wear resistance is essential for the magnetic recording medium.

Further, according to diversification of applications, remarkably high environmental resistance is required for the magnetic recording medium. Therefore, further improvement of characteristics such as reliability, particularly chemical resistance, of the lubricant forming the lubricating layer, which has a significant influence on the reliability of a magnetic disk, is required.

However, in general, when a film thickness of the lubricating layer is reduced, the lubricating layer cannot sufficiently cover the magnetic recording medium, and the chemical resistance and the wear resistance tend to deteriorate.

The present invention was made in view of the above circumstances, and an object thereof is to provide a fluorine-containing ether compound which can be suitably used as a material for a lubricant for a magnetic recording medium which can realize excellent chemical resistance and wear resistance, even when the film thickness is reduced.

In addition, another object of the present invention is to provide a lubricant for a magnetic recording medium, including the fluorine-containing ether compound of the present invention.

In addition, still another object of the present invention is to provide a magnetic recording medium which includes a lubricating layer using the fluorine-containing ether compound of the present invention and has excellent chemical resistance and wear resistance.

Solution to Problem

The present inventors have intensively studied to achieve the above objects. As a result, it was found that a fluorine-containing ether compound including an alkenyl group having 2 to 8 carbon atoms or an alkynyl group having 3 to 8 carbon atoms and a divalent linking group having a polar group at each of both ends of a perfluoropolyether chain may be used in order to achieve the above objects, thus conceiving the present invention.

That is, the present invention relates to the following aspects.

[1] A fluorine-containing ether compound represented by Formula (1).

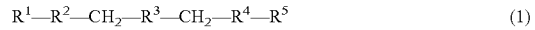

(in Formula (1), $R^1$ and $R^5$ may be the same as or different from each other and each represents an alkenyl group having 2 to 8 carbon atoms or an alkynyl group having 3 to 8 carbon atoms, $R^2$ and $R^4$ may be the same as or different from each other and each represents a divalent linking group having a polar group and $R^3$ represents a perfluoropolyether chain, with a proviso that $R^1$ and $R^2$ are, and $R^4$ and $R^5$ are divided due to the presence of an atom other than the carbon atom such as an oxygen atom.)

[2] The fluorine-containing ether compound according to [1], in which $R^1$ and $R^5$ each represents an alkenyl group having 2 to 5 carbon atoms or an alkynyl group having 3 to 5 carbon atoms.

[3] The fluorine-containing ether compound according to [2], in which $R^1$ and $R^5$ each represents one selected from the group consisting of a vinyl group, an allyl group, a 3-butenyl group, a 4-pentenyl group, a propargyl group, a 3-butynyl group, and a 4-pentynyl group.

[4] The fluorine-containing ether compound according to any one of [1] to [3], in which the polar group included in $R^2$ and $R^4$ is a hydroxy group.

[5] The fluorine-containing ether compound according to any one of [1] to [4], in which $R^2$ and $R^4$ are represented by Formula (2-1) or (2-2):

—O—(CH$_2$CH(OH)CH$_2$O)$_a$— (2-1)

(in Formula (2-1), a represents 1 to 3)

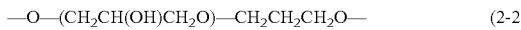

—O—(CH$_2$CH(OH)CH$_2$O)—CH$_2$CH$_2$CH$_2$O— (2-2)

(in Formula (2-2), a represents 1 to 3).

[6] The fluorine-containing ether compound according to any one of [1] to [5], in which $R^3$ is represented by any one of Formulas (3) to (5):

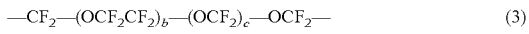

—CF$_2$—(OCF$_2$CF$_2$)$_b$—(OCF$_2$)$_c$—OCF$_2$— (3)

(in Formula (3), b and c each represents 0 to 20, but b and c are not 0 simultaneously)

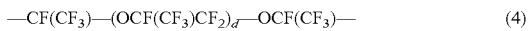

—CF(CF$_3$)—(OCF(CF$_3$)CF$_2$)$_d$—OCF(CF$_3$)— (4)

(in Formula (4), d represents 1 to 20)

—CF$_2$CF$_2$—(OCF$_2$CF$_2$CF$_2$)$_e$—OCF$_2$CF$_2$— (5)

(in Formula (5), e represents 1 to 20).

[7] The fluorine-containing ether compound according to any one of [I] to [6], in which a number average molecular weight is within a range of 500 to 10000.

[8] A lubricant for a magnetic recording medium, including the fluorine-containing ether compound according to any one of [1] to [7].

[9] A magnetic recording medium, including: a substrate; and at least a magnetic layer, a protective layer, and a lubricating layer sequentially on the substrate, in which the lubricating layer includes the fluorine-containing ether compound according to any one of [1] to [8].

[10] The magnetic recording medium according to [9], in which an average film thickness of the lubricating layer is 0.5 nm to 2 nm.

Advantageous Effects of Invention

The fluorine-containing ether compound of the present invention is a compound represented by Formula (1), and is suitable as a material of a lubricant for a magnetic recording medium.

Since the lubricant for a magnetic recording medium of the present invention includes the fluorine-containing ether compound of the present invention, it is possible to form a lubricating layer in which excellent chemical resistance and wear resistance are obtained even when the thickness is reduced.

Since the magnetic recording medium of the present invention includes a lubricating layer having excellent chemical resistance and wear resistance, it has excellent reliability and durability.

BRIEF DESCRIPTION OF DRAWINGS

FIG. 1 is a schematic sectional view showing a magnetic recording medium according to an embodiment of the present invention.

BEST MODE FOR CARRYING OUT THE INVENTION

Hereinafter, preferred examples of a fluorine-containing ether compound, a lubricant for a magnetic recording medium, and a magnetic recording medium of the present invention are described in detail. The present invention is not limited to only the embodiments shown below.

[Fluorine-Containing Ether Compound]

The fluorine-containing ether compound of the present embodiment is represented by Formula (1).

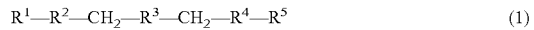

$R^1$—$R^2$—CH$_2$—$R^3$—CH$_2$—$R^4$—$R^5$ (1)

(In Formula (1), $R^1$ and $R^5$ may be the same as or different from each other and represent an alkenyl group having 2 to 8 carbon atoms or an alkynyl group having 3 to 8 carbon atoms, $R^2$ and $R^4$ may be the same as or different from each other and represent a divalent linking group having a polar group and $R^3$ represents a perfluoropolyether chain, with a proviso that $R^1$ and $R^2$ are, and $R^4$ and $R^5$ are divided due to the presence of an atom other than the carbon atom such as an oxygen atom.)

In the fluorine-containing ether compound represented by Formula (1), $R^1$ and $R^5$ each represents an alkenyl group having 2 to 8 carbon atoms or an alkynyl group having 3 to 8 carbon atoms. In the fluorine-containing ether compound of the present embodiment, the alkenyl group or the alkynyl group in $R^1$ and the polar group in $R^2$, and the alkenyl group or the alkynyl group in $R^5$ and the polar group in $R^4$ respectively exhibit favorable interaction with the protective layer, in the lubricating layer including the groups. In the fluorine-containing ether compound of the present embodiment, the alkenyl group having 2 to 8 carbon atoms or the alkynyl group having 3 to 8 carbon atoms can be appropriately selected according to performance or the like required for a lubricant for a magnetic recording medium (hereinafter, abbreviated as "lubricant" in some cases) including the fluorine-containing ether compound.

The alkenyl group having 2 to 8 carbon atoms represented by $R^1$ or $R^5$ is a group having one double bond. The alkenyl group having 2 to 8 carbon atoms represented by $R^1$ or $R^5$ is bonded to each of divalent linking groups $R^2$ and $R^4$ each having a polar group.

In a case where $R^1$ and/or $R^5$ is the alkenyl group, since the number of carbon atoms in the alkenyl group is 8 or less, an appropriate distance is formed between the alkenyl group represented by $R^1$ and the polar group of $R^2$ and/or between the alkenyl group represented by $R^5$ and the polar group of $R^4$. According to this, in the lubricating layer including these groups, favorable interaction with the protective layer is exhibited. The alkenyl group having 2 to 8 carbon atoms represented by $R^1$ or $R^5$ is not particularly limited, and examples thereof include a vinyl group, an allyl group, a crotyl group, a butenyl group, a beta-methallyl group, a methylbutenyl group, a pentenyl group, a hexenyl group, a heptenyl group, and an octenyl group. Among these, from the viewpoint of exhibiting favorable affinity to the protective layer of the magnetic recording medium, the vinyl group, the allyl group, the 3-butenyl group, and the 4-pentenyl group, which are alkenyl groups having 2 to 5 carbon atoms, are preferable, and the allyl group is particularly preferable. In a case where $R^1$ and/or $R^5$ is an alkenyl group having 3 or more carbon atoms, it is preferable that the double bond be disposed at the outermost end of the fluorine-containing ether compound. In this case, compared to a case where the double bond is disposed at a position other than the outermost end of the fluorine-containing ether compound, the interaction between the alkenyl group represented by $R^1$ and/or $R^5$ and the protective layer is easily obtained and the affinity between the lubricating layer and the protective layer becomes more favorable.

The alkynyl group having 3 to 8 carbon atoms represented by $R^1$ or $R^5$ is a group having one triple bond. The alkynyl group having 3 to 8 carbon atoms represented by $R^1$ or $R^5$ is bonded to each of the divalent linking groups $R^2$ and $R^4$ each having a polar group.

In a case where $R^1$ and/or $R^5$ is the alkynyl group, since the number of carbon atoms in the alkynyl group is 8 or less, an appropriate distance is formed between the alkynyl group represented by $R^1$ and the polar group of $R^2$ or between the alkynyl group represented by $R^5$ and the polar group of $R^4$. Accordingly, in the lubricating layer including these groups, favorable interaction with the protective layer is exhibited. The alkynyl group having 3 to 8 carbon atoms represented by $R^1$ or $R^5$ is not particularly limited, and examples thereof include a 1-propynyl group, a propargyl group, a butynyl group, a methylbutynyl group, a pentynyl group, a methylpentynyl group, a hexynyl group, a methylhexynyl group, a heptynyl group, and an octynyl group. Among these, from the viewpoint of exhibiting favorable affinity to the protective layer of the magnetic recording medium, the 1-propynyl group, the propargyl group, the butynyl group, and the pentynyl group, which are alkynyl groups having 3 to 5 carbon atoms, are preferable, and the propargyl group is particularly preferable. In addition, the alkynyl group may be in a form that an alkenyl group is included in a molecule, such as a vinylpentynyl group. In a case where $R^1$ and/or $R^5$ is an alkynyl group having 3 or more carbon atoms, it is preferable that the triple bond be disposed at the outermost end of the fluorine-containing ether compound. In this case, compared to a case where the triple bond is disposed at a position other than the outermost end of the fluorine-containing ether compound, the interaction between the alkynyl group of $R^1$ and/or $R^5$ and the protective layer is easily obtained and the affinity between the lubricating layer and the protective layer becomes more favorable.

$R^2$ and $R^4$ in Formula (1) each represents a divalent linking group having a polar group. $R^2$ and $R^4$ may be the same as or different from each other. Since $R^2$ and $R^4$ each have a polar group, in a case where the lubricating layer is formed on the protective layer by using a lubricant including the fluorine-containing ether compound of the present embodiment, favorable interaction occurs between the lubricating layer and the protective layer. The divalent linking group having a polar group can be appropriately selected according to performance or the like required for the lubricant including the fluorine-containing ether compound.

The divalent linking group in $R^2$ and $R^4$ is a divalent linking group having at least one polar group.

It is necessary to select the polar group, so that the polar group can cause a favorable interaction between the lubricant and the protective layer when the lubricating layer generated from the lubricant including the fluorine-containing ether compound is formed on the protective layer. Examples of such a polar group include a hydroxyl group (a hydroxy group) (—OH), an amino group (—NH$_2$), a carboxyl group (—COOH), an aldehyde group (—CHO), a carbonyl group (—CO—), and a sulfonic acid group (—SO$_3$H). Among these, the hydroxyl group is particularly preferable. The hydroxyl group strongly interacts with the protective layer, particularly with the carbon-based protective layer, to increase adhesion between the lubricating layer and a surface of the protective layer.

Each of $R^2$ and $R^4$ is preferably a divalent linking group represented by Formula (2-1) or (2-2). In Formula (2-2), it is preferable that the right side be an $R^1$ or $R^5$ side.

(2-1)

(In Formula (2-1), a represents 1 to 3.)

(2-2)

(In Formula (2-2), a represents 1 to 3.)

Since a in Formulas (2-1) and (2-2) is 1 to 3, an interaction between the polar group in $R^2$ and $R^4$ and the surface of the protective layer is obtained. Therefore, in addition to the interaction between the alkenyl group having 2 to 8 carbon atoms or the alkynyl group having 3 to 8 carbon atoms represented by $R^1$ or $R^5$ and the surface of the protective layer, an interaction between the polar group in $R^2$ and $R^4$ and the surface of the protective layer becomes stronger and the affinity between the lubricating layer and the protective layer becomes more favorable.

If a shown in Formula (2-2) is 3 or less, the polarity of the polar group does not become too high, and pickup, which is adhesion to a magnetic head as a foreign substance (smear), is difficult to occur. The aforementioned a may be any integer of 1, 2 or 3.

In addition, in the fluorine-containing ether compound, a carbon atom such as a carbon atom and an oxygen atom which are bonded to each other in a chain shape (at least —O—CH$_2$—) are disposed between the bonding carbon atom in the alkenyl group having 2 to 8 carbon atoms or the alkynyl group having 3 to 8 carbon atoms represented by $R^1$ or $R^5$ and a carbon atom to which the polar group is bonded in $R^2$ or $R^4$. Therefore, for example, compared to a case where a polar group to be used in $R^2$ (or $R^4$) is directly bonded to a carbon of $R^1$ (or $R^5$) on a side closest to $R^2$ (or $R^4$), the interaction between the alkenyl group having 2 to 8 carbon atoms or the alkynyl group having 3 to 8 carbon atoms and the polar group is weakened. On the other hand, the interaction of $R^1$ or $R^5$ and the polar group in $R^2$ or $R^4$ with many functional groups present on the surface of the protective layer is relatively high compared to the case where the polar group to be used in $R^2$ (or $R^4$) is directly bonded to the carbon of $R^1$ (or $R^5$) on a side closest to $R^2$ (or $R^4$). As a result, in a case where the lubricating layer is formed on the protective layer by using the lubricant including the fluorine-containing ether compound, the adhesion between the lubricating layer and the surface of the protective layer increases.

Therefore, in a case where $R^2$ and $R^4$ each represents a divalent linking group represented by Formula (2-1) or (2-2), the lubricating layer formed by using the lubricant including the fluorine-containing ether compound becomes a layer having more excellent chemical resistance and wear resistance. From the viewpoint of affinity between the lubricating layer and the protective layer, it is desirable that a total number of the carbon atom and the oxygen atom which are bonded to each other in a chain shape is 2 to 4, which are present between the alkenyl group having 2 to 8 carbon atoms or the alkynyl group having 3 to 8 carbon atoms represented by $R^1$ or $R^5$ and the carbon atom to which the polar group is bonded in $R^2$ or $R^4$.

$R^3$ represents a perfluoropolyether chain (hereinafter, abbreviated as "PFPE chain" in some cases). In the lubricating layer including the fluorine-containing ether compound of the present embodiment, the PFPE chain covers the surface of the protective layer and reduces a frictional force between the magnetic head and the protective layer. The PFPE chain is appropriately selected according to performance or the like required for the lubricant including the fluorine-containing ether compound.

Examples of the PFPE chain include a perfluoromethylene oxide polymer, a perfluoroethylene oxide polymer, a perfluoro-n-propylene oxide polymer, a perfluoroisopropylene oxide polymer, and the like, a chain based on these polymers, and a chain including a copolymer of these polymers.

Specifically, $R^3$ is preferably one represented by any one of Formulas (3) to (5). If $R^3$ is one of these PFPE chains, the lubricating layer including the lubricant including the fluorine-containing ether compound exhibits favorable lubricity.

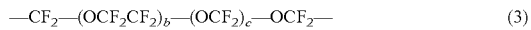  (3)

(In Formula (3), b and c each represents 0 to 20, but b and c are not 0 simultaneously.)

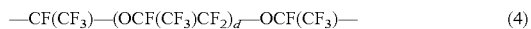  (4)

(In Formula (4), d represents 1 to 20.)

  (5)

(In Formula (5), e represents 1 to 20.)

In Formula (3), b and c each represents 0 to 20. In Formula (4), d represents 1 to 20. In Formula (5), e represents 1 to 20. b and c may be selected from integers selected from 0 and 1 to 20, or each may be a number after the decimal point. d and e each may be an integer selected from 1 to 20. b, c, d, and e each may be selected according to a required characteristic as needed. For example, according to the required characteristic, it is preferable to be 0 to 15, and also preferable to be 0 to 10, 0 to 8, or 1 to 8. As the PFPE chain of the fluorine-containing ether compound applied on the protective layer is shorter, the lubricating layer having a thinner film thickness can be formed on the protective layer. Therefore, it is more preferable that b and c each represents 0 to 7 and d and e each represents 1 to 7. Further, it is particularly preferable that b represent 3 to 7, c represent 0 to 5, and d and e each represents 4 to 7.

If b, c, d, and e are 20 or less, since viscosity of the fluorine-containing ether compound does not become too high, the lubricant including the fluorine-containing ether compound is not difficult to be applied.

In the fluorine-containing ether compound represented by Formula (1), $R^1$ and $R^5$ may be different from or the same as each other. From the viewpoint that the fluorine-containing ether compound represented by Formula (1) can be easily produced, it is preferable that $R^1$ and $R^5$ be the same as each other.

In addition, in the fluorine-containing ether compound represented by Formula (1), $R^2$ and $R^4$ may be different from or the same as each other. From the viewpoint that the fluorine-containing ether compound represented by Formula (1) can be easily produced, it is preferable that $R^2$ and $R^4$ be the same as each other.

Therefore, when $R^1$ and $R^5$ of the fluorine-containing ether compound represented by Formula (I) are the same as each other, and $R^2$ and $R^4$ are the same as each other, the fluorine-containing ether compound represented by Formula (1) can be more easily produced.

Specifically, it is preferable that the fluorine-containing ether compound of the present embodiment be any of compounds represented by Formulas (A) to (J). In the compounds represented by Formulas (A) to (J), $R^1$ and $R^5$ each have an alkenyl group having 2 to 5 carbon atoms or an alkynyl group having 3 to 5 carbon atoms, $R^2$ and $R^4$ each represents a linking group represented by Formula (2-1), and $R^3$ represents the PFPE chain represented by Formula (3). Since the number of f, g, and the like represents an average value, the number is not necessarily an integer.

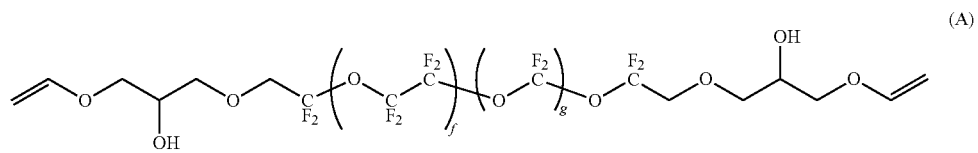

(A)

(In Formula (A), f and g each represents 0 to 7, but f and g are not 0 simultaneously.)

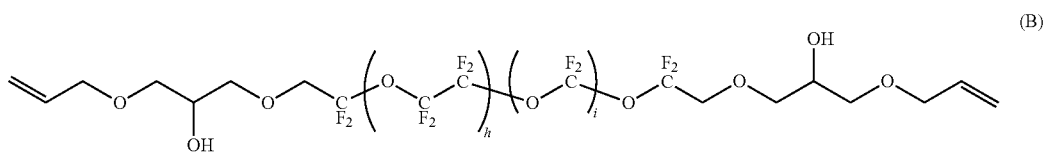

(B)

(In Formula (B), h and i each represents 0 to 7, but h and i are not 0 simultaneously.)

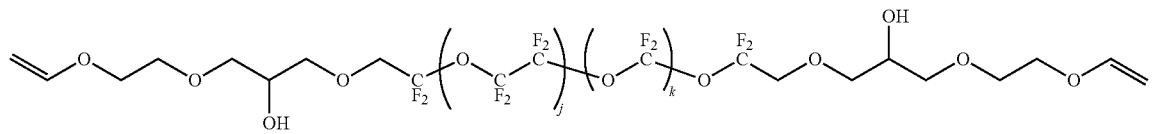

(C)

(In Formula (C), j and k each represents 0 to 7, but j and k are not 0 simultaneously.)

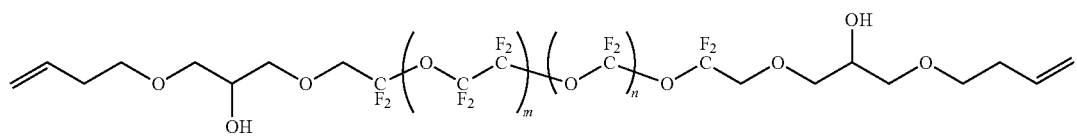

(D)

(In Formula (D), m and n each represents 0 to 7, but m and n are not 0 simultaneously.)

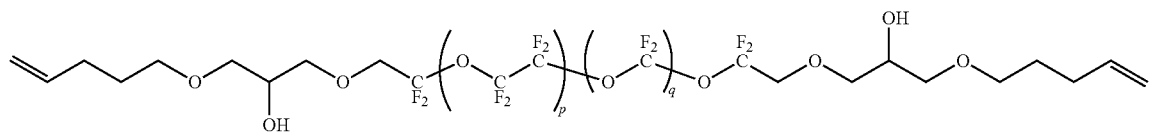

(E)

(In Formula (E), p and q each represents 0 to 7, but p and q are not 0 simultaneously.)

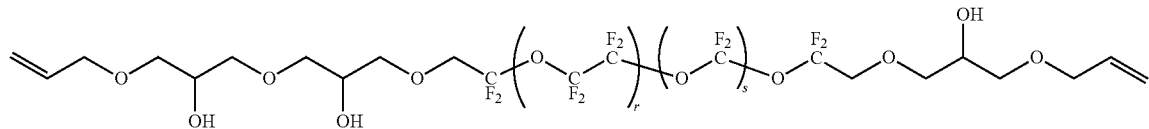

(F)

(In Formula (F), r and s each represents 0 to 7, but r and s are not 0 simultaneously.)

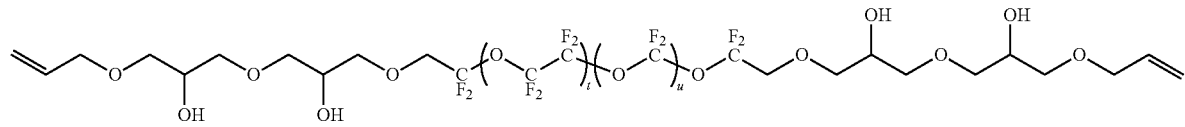

(G)

(In Formula (G), t and u each represents 0 to 7, but t and u are not 0 simultaneously.)

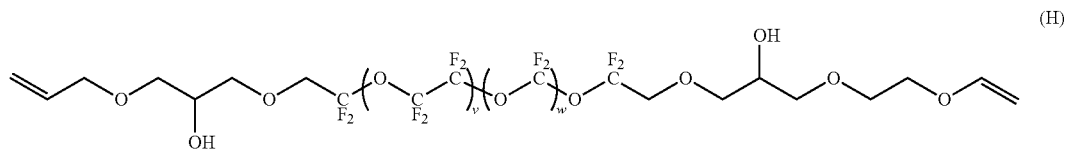
(H)

(In Formula (H), v and w each represents 0 to 7, but v and w are not 0 simultaneously.)

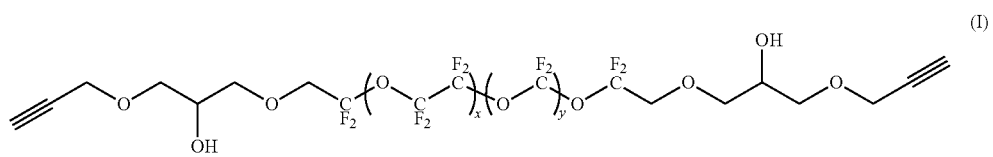
(I)

(In Formula (I), x and y each represents 0 to 7, but x and y are not 0 simultaneously.)

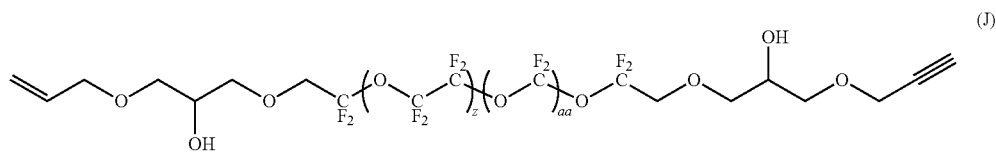
(J)

(In Formula (J), z and aa each represents 0 to 7, but z and aa are not 0 simultaneously.)

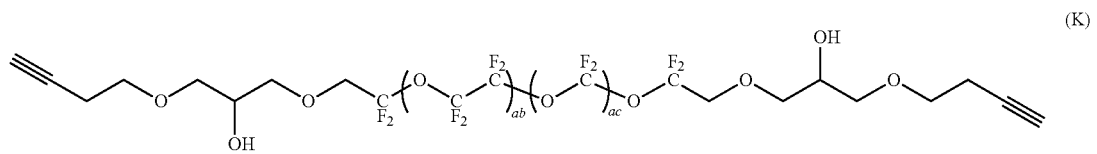
(K)

(In Formula (K), ab and ac each represents 0 to 7, but ab and ac are not 0 simultaneously.)

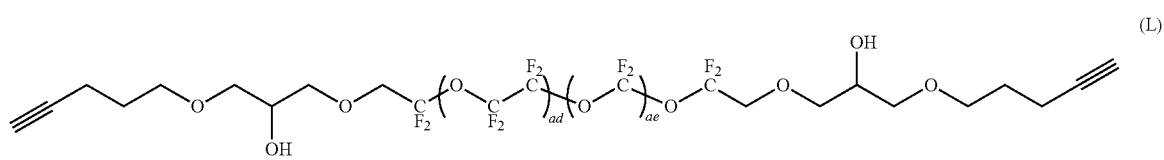
(L)

(In Formula (L), ad and ae each represents 0 to 7, but ad and ae are not 0 simultaneously.)

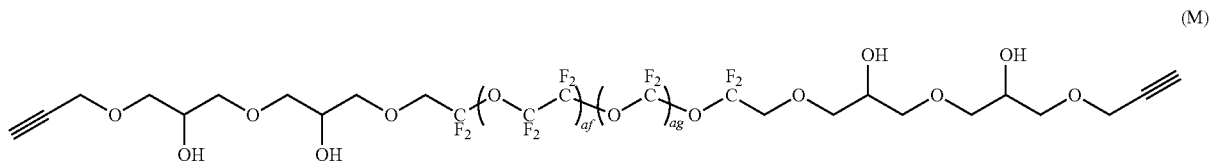

(M)

(In Formula (M), af and ag each represents 0 to 7, but af and ag are not 0 simultaneously.)

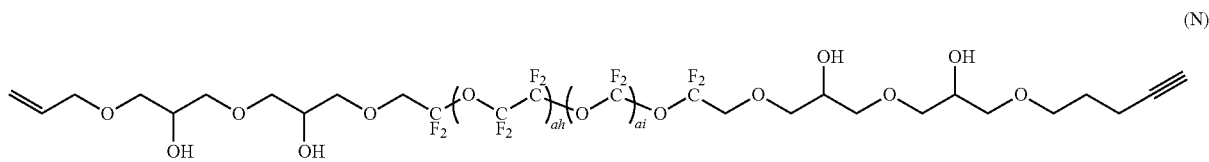

(N)

(In Formula (N), ah and ai each represents 0 to 7, but ah and ai are not 0 simultaneously.)

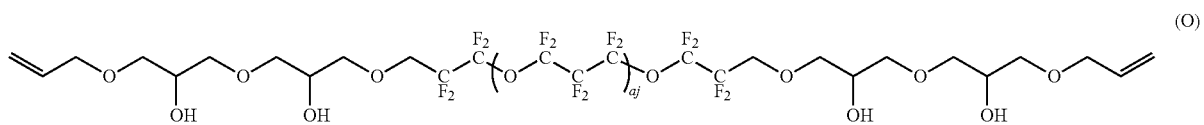

(O)

(In Formula (0), aj represents 1 to 7.)

f, g, h, i, j, k, m, n, p, q, r, s, t, u, v, w, x, y, z, aa, ab, ac, ad, ae, af, ag, ah, and ai each represents 0 to 7, but preferable ranges may be changed according to the required characteristic. These may not be integers. For example, these may be 0 to 6, 1 to 6, or may also be in a range of 0 to 1, 0 to 2, 2 to 5, 3 to 5, or 3 to 6. aj represents 1 to 7, but preferable range may be changed according to the required characteristic. This may not be an integer. For example, this may be 1 to 6, or may also be in a range of 1 to 2, 1 to 3, or 3 to 5.

In the fluorine-containing ether compound of the present embodiment, a number average molecular weight (Mn) is preferably within a range of 500 to 10000, more preferably within a range of 750 to 7500, and particularly preferably within a range of 1000 to 5000.

When the number average molecular weight is 500 or more, the lubricating layer including the lubricant including the fluorine-containing ether compound of the present embodiment becomes to have excellent heat resistance. The number average molecular weight of the fluorine-containing ether compound is more preferably 1000 or more. In addition, when the number average molecular weight is 10000 or less, the viscosity of the fluorine-containing ether compound is appropriate, and when applying a lubricant containing the compound, a lubricating layer having a reduced film thickness can be easily formed. The number average molecular weight of the fluorine-containing ether compound is preferably 5000 or less, from the viewpoint that the viscosity capable of easy handling is obtained in a case of being applied to a lubricant.

The number average molecular weight (Mn) of the fluorine-containing ether compound is a value measured by $^1$H-NMR and $^{19}$F-NMR using AVANCE 111400 manufactured by Bruker Biospin. Specifically, the number of repetition units of the PFPE chain was calculated from an integral value measured by $^{19}$F-NMR, and the number average molecular weight was determined. In addition, since the number of repetition units represents an average value, it may be represented by a number after a decimal point in some cases. In the measurement of NMR (nuclear magnetic resonance), a sample was diluted in hexafluorobenzene/d-acetone (4/1 v/v) solvent to be used for the measurement. For the standard of $^{19}$F-NMR chemical shift, a peak of the hexafluorobenzene was set to −164.7 ppm. For the standard of $^1$H-NMR chemical shift, a peak of the acetone was set to 2.2 ppm.

A molecular weight dispersity (ratio shown by weight average molecular weight (Mw)/number average molecular weight (Mn)) is preferably set to 1.3 or less, by performing molecular weight fractionation on the fluorine-containing ether compound of the present embodiment by an appropriate method.

In the present embodiment, the molecular weight fractionation method is not particularly limited. For example, molecular weight fractionation by silica gel column chromatography or gel permeation chromatography (GPC) method, molecular weight fractionation by supercritical extraction method, and the like can be used.

The fluorine-containing ether compound of the present embodiment includes a perfluoropolyether chain in a structure, and includes an alkenyl group having 2 to 8 carbon atoms or an alkynyl group having 3 to 8 carbon atoms at the end of a molecule and a divalent linking group having a polar group. When combining the alkenyl group having 2 to 8 carbon atoms or the alkynyl group having 3 to 8 carbon atoms with the divalent linking group having a polar group, a lubricating layer in which affinity to the surface of the protective layer is high and coverage is high even in a case of a thin film can be formed. A magnetic recording medium including such a lubricating layer can guarantee sufficient long-term reliability.

In the fluorine-containing ether compound of the present embodiment, the alkenyl group having 2 to 8 carbon atoms or the alkynyl group having 3 to 8 carbon atoms at the end of the molecule is separated from the polar group included in the linking group, and intramolecular interaction (affinity) with each other is relatively low. Therefore, it is considered that in the alkenyl group having 2 to 8 carbon atoms or the alkynyl group having 3 to 8 carbon atoms at the end of the molecule, an unsaturated it bond thereof can strengthen adsorption with the carbon protective film having the n bonds as well in a large number. It is also considered that the polar group can relatively strengthen interaction with functional groups present in a large number on the surface of the protective layer to increase the affinity to the protective layer.

In this case, from the viewpoint of the affinity to the protective layer, the shortest distance between the alkenyl group having 2 to 8 carbon atoms or the alkynyl group having 3 to 8 carbon atoms and the polar group is desirably set so that they are separated by a distance of three atoms or more.

"Production Method"

A production method of the fluorine-containing ether compound of the present embodiment is not particularly limited, and a known production method can be used for the production. The fluorine-containing ether compound of the present embodiment can be produced, for example, using the following production method.

Examples of the production method of the fluorine-containing ether compound of the present embodiment include a method in which a compound including an epoxy group and an alkenyl group or an alkynyl group is reacted in two equivalent amounts to a perfluoropolyether compound having a perfluoropolyether chain in a molecule and having a hydroxy group at the end of the molecule. Examples of the compound having the epoxy group and the alkenyl group or the alkynyl group include compounds represented by Formulas (6) to (16).

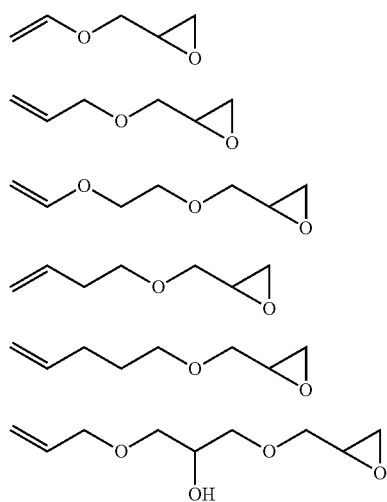

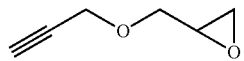

(12)

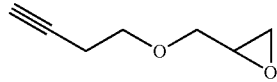

(13)

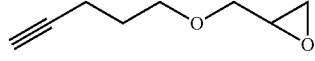

(14)

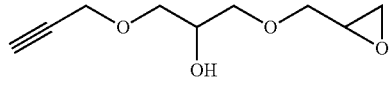

(15)

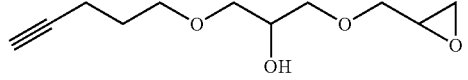

(16)

The fluorine-containing ether compound of the present embodiment is a compound in which the alkenyl group having 2 to 8 carbon atoms or the alkynyl group having 3 to 8 carbon atoms represented by $R^1$ or $R^5$ is bonded to each of both ends of the PFPE chain represented by $R^3$, via the divalent linking group having a polar group represented by $R^2$ or $R^4$, as shown in Formula (1). In the lubricating layer including the fluorine-containing ether compound of the present embodiment, the PFPE chain covers the surface of the protective layer and reduces a frictional force between the magnetic head and the protective layer. Thus, the combination of $R^2$, $R^4$, $R^1$, and $R^5$, disposed at both ends of the PFPE chain, with the PFPE chain improves the affinity between the lubricating layer including the fluorine-containing ether compound of the present embodiment and the protective layer. As a result, in a case where a lubricating layer is formed on the protective layer of the magnetic recording medium by using the lubricant including the fluorine-containing ether compound of the present embodiment, even when the film thickness is reduced, high coverage is obtained, and it is possible to form a lubricating layer having excellent chemical resistance and wear resistance.

[Lubricant for Magnetic Recording Medium]

The lubricant for a magnetic recording medium of the present embodiment includes the fluorine-containing ether compound represented by Formula (1).

The lubricant of the present embodiment can be used by being mixed with a known material used as a lubricant material as needed, within a range not impairing the characteristics obtained by including the fluorine-containing ether compound represented by Formula (1).

Specific examples of the known material include FOMBLIN (registered trademark) ZDIAC, FOMBLIN ZDEAL, and FOMBLIN AM-2001 (all manufactured by Solvay Solexis), and Moresco A20H (manufactured by Moresco).

In the known material used by being mixed with the lubricant of the present embodiment, a number average molecular weight is preferably 1000 to 10000.

In a case where the lubricant of the present embodiment includes other materials in addition to the fluorine-containing ether compound represented by Formula (1), a content of the fluorine-containing ether compound represented by Formula (1) in the lubricant of the present embodiment is preferably 50% by mass or more, more preferably 60% by mass or more, and still more preferably 70% by mass or more, relative to a total amount of the lubricant. It is also preferably 80% by mass or more or 90% by mass.

Since the lubricant of the present embodiment includes the fluorine-containing ether compound represented by Formula (1), even if the film thickness is reduced, the surface of the protective layer can be covered with high coverage, and it is possible to form a lubricating layer with excellent chemical resistance and wear resistance.

[Magnetic Recording Medium]

The magnetic recording medium of the present embodiment is obtained by providing at least a magnetic layer, a protective layer, and a lubricating layer sequentially on a substrate.

In the magnetic recording medium of the present embodiment, one or more base layers can be provided between the substrate and the magnetic layer, as needed. In addition, at least one of an adhesion layer and a soft magnetic layer can be provided between the base layer and the substrate.

FIG. 1 is a schematic sectional view showing the magnetic recording medium according to an embodiment of the present invention.

A magnetic recording medium 10 of the present embodiment has a structure in which an adhesion layer 12, a soft magnetic layer 13, a first base layer 14, a second base layer 15, a magnetic layer 16, a protective layer 17, and a lubricating layer 18 are sequentially provided on a substrate 11.

"Substrate"

For example, a nonmagnetic substrate or the like in which a film made of NiP or an NiP alloy is formed on a base substance made of metal or alloy material such as Al or an Al alloy can be used as the substrate 11.

In addition, as the substrate 11, a nonmagnetic substrate made of a nonmetallic material such as glass, ceramics, silicon, silicon carbide, carbon, or resin may be used, and a nonmagnetic substrate in which a film of NiP or an NiP alloy is formed on a base substance made of the nonmetallic materials may also be used.

The glass substrate has rigidity and is excellent in smoothness. Therefore, the glass substrate is suitable for high recording density. Examples of the glass substrate include an aluminosilicate glass substrate. In particular, a chemically strengthened aluminosilicate glass substrate is suitable.

A roughness of a main surface of the substrate 11 is preferably ultra-smooth in which Rmax is 6 nm or less and Ra is 0.6 nm or less. Here, the surface roughness Rmax and Ra are based on the definition of JIS B 0601.

"Adhesion Layer"

The adhesion layer 12 prevents corrosion of the substrate 11 from progressing, which occurs in a case where the substrate 11 and the soft magnetic layer 13, which is provided on the adhesion layer 12, are disposed in contact with each other.

A material of the adhesion layer 12 can be appropriately selected from, for example, Cr, a Cr alloy, Ti, a Ti alloy, CrTi, NiAl, and an AlRu alloy. The adhesion layer 12 can be formed, for example, by a sputtering method.

"Soft Magnetic Layer"

The soft magnetic layer 13 preferably has a structure in which a first soft magnetic film, an intermediate layer which is a Ru film, and a second soft magnetic film are sequentially laminated. That is, the soft magnetic layer 13 preferably has a structure in which the intermediate layer which is the Ru film is sandwiched between the two soft magnetic films to couple the soft magnetic films above and below the intermediate layer by anti-ferro coupling (AFC).

Examples of materials of the first soft magnetic film and the second soft magnetic film include a CoZrTa alloy and a CoFe alloy.

It is preferable to add any of Zr, Ta, and Nb to the CoFe alloy used for the first soft magnetic film and the second soft magnetic film. Accordingly, amorphization of the first soft magnetic film and the second soft magnetic film is promoted. An orientation of the first base layer (seed layer) can be improved, and flying height of a magnetic head can be reduced.

The soft magnetic layer 13 can be formed, for example, by a sputtering method.

"First Base Layer"

The first base layer 14 is a layer for controlling the orientation or a crystal size of the second base layer 15 and the magnetic layer 16 provided thereon.

Examples of the first base layer 14 include a Cr layer, a Ta layer, a Ru layer, or a layer of a CrMo alloy, a CoW alloy, a CrW alloy, a CrV alloy, or a CrTi alloy.

The first base layer 14 can be formed, for example, by a sputtering method.

"Second Base Layer"

The second base layer 15 is a layer that controls the orientation of the magnetic layer 16 to be favorable. The second base layer 15 is preferably a layer made of Ru or a Ru alloy.

The second base layer 15 may be a layer formed by a single layer or may be formed of a plurality of layers. In a case where the second base layer 15 is formed of a plurality of layers, all the layers may be formed of the same material, or at least one layer may be formed of a different material.

The second base layer 15 can be formed, for example, by a sputtering method.

"Magnetic Layer"

The magnetic layer 16 is formed of a magnetic film in which an easy axis of magnetization is oriented in a direction perpendicular or horizontal to a substrate surface. The magnetic layer 16 is preferably a layer including Co and Pt. and in order to further improve an SNR characteristic, it may be a layer including at least one selected from oxides, Cr, B, Cu, Ta, and Zr.

Examples of the oxide included in the magnetic layer 16 include $SiO_2$, $SiO$, $Cr_2O_3$, $CoO$, $Ta_2O_3$, and $TiO_2$.

The magnetic layer 16 may be a layer formed by a single layer or may be formed of a plurality of magnetic layers including a material having a different composition.

For example, in a case where the magnetic layer 16 is formed of three layers that are a first magnetic layer, a second magnetic layer, and a third magnetic layer, the first magnetic layer preferably has a granular structure that includes Co, Cr, and Pt, and further includes an oxide. As the oxide included in the first magnetic layer, for example, oxides of Cr, Si, Ta, Al, Ti, Mg, Co, and the like are preferably used. Among these, in particular, $TiO_2$, $Cr_2O_3$, $SiO_2$, and the like can be suitably used. In addition, it is preferable that the first magnetic layer includes a complex oxide obtained by adding two or more kinds of oxides. Among these, in particular, $Cr_2O_3$—$SiO_2$, $Cr_2O_3$—$TiO_2$, and $SiO_2$—$TiO_2$ can be suitably used.

The first magnetic layer can include at least one element selected from the group consisting of B, Ta, Mo, Cu, Nd, W, Nb, Sm, Tb, Ru, and Re, in addition to Co, Cr, Pt, and the oxide.

For the second magnetic layer, the same material as the first magnetic layer can be used. The second magnetic layer preferably has a granular structure.

The third magnetic layer preferably has a non-granular structure including a material that includes Co, Cr, and Pt and does not include an oxide. The third magnetic layer can include at least one element selected from the group consisting of B, Ta, Mo, Cu, Nd, W, Nb, Sm, Th, Ru, Re, and Mn, in addition to Co, Cr, and Pt.

In a case where the magnetic layer 16 is formed of a plurality of magnetic layers, it is preferable to provide a nonmagnetic layer between adjacent magnetic layers. In a case where the magnetic layer 16 is formed of three layers that are the first magnetic layer, the second magnetic layer, and the third magnetic layer, a nonmagnetic layer is preferably provided between the first magnetic layer and the second magnetic layer and between the second magnetic layer and the third magnetic layer.

For the nonmagnetic layer provided between the adjacent magnetic layers of the magnetic layer 16, for example, Ru, a Ru alloy, a CoCr alloy, and CoCrX1 alloy (X1 represents at least one element selected from the group consisting of Pt, Ta, Zr, Re, Ru, Cu, Nb, Ni, Mn, Ge, Si, O, N, W, Mo, Ti, V, Zr, and B) can be suitably used.

For the nonmagnetic layer provided between the adjacent magnetic layers of the magnetic layer 16, it is preferable to use an alloy material including an oxide, a metal nitride, or a metal carbide. Specifically, as the oxide, for example, $SiO_2$, $Al_2O_3$, $Ta_2O_5$, $Cr_2O_3$, MgO, $Y_2O_3$, and $TiO_2$ can be used. As the metal nitride, for example, AlN, $Si_3N_4$, TaN, and CrN can be used. As the metal carbide, for example, TaC, BC, and SiC can be used.

The nonmagnetic layer can be formed, for example, by a sputtering method.

In order to realize higher recording density, the magnetic layer 16 is preferably a magnetic layer for perpendicular magnetic recording in which the easy axis of magnetization is perpendicular to the substrate surface, but may also be an in-plane magnetic recording.

The magnetic layer 16 may be formed by a vapor deposition method, an ion beam sputtering method, a magnetron sputtering method, and any known method of the related art, and is usually formed by the sputtering method.

"Protective Layer"

The protective layer 17 is a layer for protecting the magnetic layer 16. The protective layer 17 may be a layer formed by a single layer or may be formed of a plurality of layers. As the protective layer 17, a carbon-based protective layer can be preferably used, and in particular, an amorphous carbon protective layer is preferable. It is preferable that the protective layer 17 be the carbon-based protective layer, from the viewpoint that the interaction with the polar group (particularly, a hydroxyl group) included in the fluorine-containing ether compound in the lubricating layer 18 is further enhanced.

The adhesion force between the carbon-based protective layer and the lubricating layer 18 can be controlled by using the carbon-based protective layer which includes hydrogenated carbon and/or nitrogenated carbon and adjusting a hydrogen content and/or a nitrogen content in the carbon-based protective layer. The hydrogen content in the carbon-based protective layer is preferably 3 atom % to 20 atom % as measured by hydrogen forward scattering (HFS). In addition, the nitrogen content in the carbon-based protective layer is preferably 4 atom % to 15 atom % as measured by X-ray photoelectron spectroscopy (XPS).

Hydrogen and/or nitrogen included in the carbon-based protective layer need not be uniformly contained throughout the carbon-based protective layer. For example, the carbon-based protective layer is, for example, a composition gradient layer in which the nitrogen is contained on the lubricating layer 18 side of the protective layer 17 and the hydrogen is contained on the magnetic layer 16 side of the protective layer 17. In this case, the adhesion force between the magnetic layer 16 and the carbon-based protective layer and between the lubricating layer 18 and the carbon-based protective layer is further enhanced.

A film thickness of the protective layer 17 is preferably 1 nm to 7 nm. When the film thickness of the protective layer 17 is 1 nm or more, performance as the protective layer 17 is sufficiently obtained. It is preferable that the film thickness of the protective layer 17 be 7 nm or less, from the viewpoint of thinning the protective layer 17.

As the film forming method of the protective layer 17, a sputtering method using a target material containing carbon, a chemical vapor deposition (CVD) method using a hydrocarbon raw material such as ethylene or toluene, an ion beam deposition (IBD) method, or the like can be used.

In a case of forming the carbon-based protective layer as the protective layer 17, a film can be formed, for example, by a DC magnetron sputtering method. In particular, in a case of forming the carbon-based protective layer as the protective layer 17, it is preferable to form an amorphous carbon protective layer by a plasma CVD method. The amorphous carbon protective layer formed by the plasma CVD method has a uniform surface and small roughness.

"Lubricating Layer"

The lubricating layer 18 prevents the magnetic recording medium 10 from being contaminated. In addition, the lubricating layer 18 reduces a frictional force of a magnetic head of a magnetic recording and reproducing apparatus sliding on the magnetic recording medium 10, and improves durability of the magnetic recording medium 10.

As shown in FIG. 1, the lubricating layer 18 is formed on and in contact with the protective layer 17. The lubricating layer 18 is formed by applying the lubricant for a magnetic recording medium of the embodiment described above onto the protective layer 17. Therefore, the lubricating layer 18 includes the fluorine-containing ether compound described above.

In a case where the protective layer 17 disposed under the lubricating layer 18 is the carbon-based protective layer, in particular, the lubricating layer 18 is bonded to the fluorine-containing ether compound included in the protective layer 17 with high bonding strength. As a result, even when the thickness of the lubricating layer 18 is reduced, the magnetic recording medium 10 in which the surface of the protective layer 17 is covered with high coverage is easily obtained, and it is possible to effectively prevent the surface of the magnetic recording medium 10 from being contaminated.

A predetermined average film thickness of the lubricating layer 18 can be selected, but the average film thickness is preferably, for example, 0.5 nm (5 Å) to 2 nm (20 Å).

When the average film thickness of the lubricating layer 18 is 0.5 nm or more, the lubricating layer 18 is formed in a uniform film thickness without being in an island form or a mesh form. Therefore, the surface of the protective layer 17 can be covered with high coverage, by the lubricating layer 18. In addition, when setting the average film thickness of the lubricating layer 18 to 2 nm or less, the lubricating layer 18 can be sufficiently thinned, and the flying height of the magnetic head can be sufficiently reduced.

"Forming Method of Lubricating Layer"

In order to form the lubricating layer 18, for example, a method in which a magnetic recording medium in the middle of production, at which each layer up to the protective layer 17 is formed on the substrate 11, is prepared, and the lubricating layer forming solution is applied onto the protective layer 17, can be used.

The lubricating layer forming solution can be produced by a predetermined method, for example, is obtained by dispersing and dissolving the lubricant for a magnetic recording medium of the embodiment in a solvent as needed to set a viscosity and concentration suitable for a coating method.

Examples of the solvent used for the lubricating layer forming solution include a fluorinated solvent such as Vertrel (registered trademark) XF (trade name, manufactured by Du Pont-Mitsui Fluorochemicals Co., Ltd.).

The coating method of the lubricating layer forming solution is not specifically limited, and examples thereof include a spin coat method, a spray method, a paper coat method, and a dip method.

In a case of using the dip method, for example, the following method can be used. First, the substrate 11 in which each layer up to the protective layer 17 is formed is immersed in the lubricating layer forming solution contained in an immersion tank of a dip coating apparatus. Then, the substrate 11 is pulled up from the immersion tank at a predetermined speed.

In this way, the lubricating layer forming solution is applied to the surface on the protective layer 17 of the substrate 11.

By using the dip method, the lubricating layer forming solution can be uniformly applied to the surface of the protective layer 17, and the lubricating layer 18 can be formed on the protective layer 17 with uniform film thickness.

In the present embodiment, it is preferable to carry out a heat treatment on the substrate 11 in which the lubricating layer 18 is formed. By applying the heat treatment, the adhesion between the lubricating layer 18 and the protective layer 17 improves, and the adhesion force between the lubricating layer 18 and the protective layer 17 improves. A predetermined heat treatment temperature can be selected, but the heat treatment temperature is preferably, for example, 100° C. to 180° C. When the heat treatment temperature is 100° C. or higher, an effect of improving the adhesion between the lubricating layer 18 and the protective layer 17 is sufficiently obtained. In addition, when the heat treatment temperature is set to be 180° C. or lower, it is possible to prevent the lubricating layer 18 from being thermally decomposed. Heat treatment time is preferably 10 minutes to 120 minutes.

In the present embodiment, in order to further enhance the adhesion force of the lubricating layer 18 to the protective layer 17, irradiation treatment with ultraviolet light (UV) on the lubricating layer 18 of the substrate 11 before or after the heat treatment may also be performed.

In addition, according to the fluorine-containing ether compound of the present embodiment, a thickness of a monomolecular film is considered to be 0.7 nm (7 Å) to 0.9 nm (9 Å) from the film thickness-surface free energy plot. In a thin film region of 1.2 nm (12 Å) or less, sufficient overlap between molecules cannot be expected. Therefore, in the heat treatment or the UV treatment, it is considered that there is no polymerization or crosslinking, which is a reaction between functional groups, and the interaction with the protective layer is strong.

The magnetic recording medium 10 of the present embodiment is obtained by providing at least the magnetic layer 16, the protective layer 17, and the lubricating layer 18 sequentially on the substrate 11. In the magnetic recording medium 10 of the present embodiment, the lubricating layer 18 including the fluorine-containing ether compound described above is formed on and in contact with the protective layer 17. The lubricating layer 18 has excellent chemical resistance and wear resistance even when the film thickness is reduced. Accordingly, the magnetic recording medium 10 of the present embodiment is excellent in reliability, in particular, suppression of silicon contamination and wear resistance. Therefore, the magnetic recording medium 10 of the present embodiment has a low flying height (for example, 10 nm or less) of the magnetic head, and has high reliability wherein operation can be performed stably over a long period even under severe environment associated with diversification of applications. Therefore, the magnetic recording medium 10 of the present embodiment is particularly suitable as a magnetic disk mounted on a load unload (LUL) type magnetic disk unit.

EXAMPLES

Hereinafter, the present invention will be further specifically described, using Examples and Comparative Examples. The present invention is not limited to only the following Examples.

Example 1

According to the method shown below, a compound represented by Formula (B) (in Formula (B), h represents 4.5 and i represents 4.5) was obtained. Hereinafter, the compound represented by Formula (B) is referred to as a compound (B).

20 g of fluoropolyether (number average molecular weight of 1000 and molecular weight distribution of 1.1) represented by $HOCH_2CF_2O(CF_2CF_2O)_h(CF_2O)_i CF_2CH_2OH$ (in the formula, h represents 4.5 and i represents 4.5) and 2.51 g of a compound represented by Formula (7), and 20 mL of t-butanol were put into a 200 mL eggplant flask under nitrogen atmosphere, and stirred at room temperature to be homogeneous.

0.90 g of potassium tert-butoxide was added to the homogeneous solution, and stirred at 70° C. for 8 hours to be reacted. The obtained reaction product was cooled to 25° C., neutralized with 1 mol/L of hydrochloric acid, and extracted with Vertrel XF manufactured by Du Pont-Mitsui Fluorochemicals Co., Ltd. (hereinafter, abbreviated as "Vertrel XF" in some cases), and washing was performed with water. An organic layer was dehydrated with anhydrous sodium sulfate and the desiccant was filtered off. Thereafter, a filtrate was concentrated. A residue was purified by silica gel column chromatography to obtain the compound (B).

$^1$H-NMR and $^{19}$F-NMR measurements of the obtained compound (B) were conducted, and a structure was identified from the following results.

$^1$H-NMR (acetone-D$_6$): δ [ppm]=3.40 to 3.55 (4H), 3.65 to 3.75 (2H), 3.75 to 3.85 (4H), 4.00 to 4.15 (8H), 5.10 to 5.15 (2H), 5.25 to 5.30 (2H), 5.85 to 5.95 (2H)

$^{19}$F-NMR (acetone-D$_6$): δ [ppm]=−51.5 to −55.5 (9F), −78.5 (2F), −80.5 (2F), −88.5 to −91.0 (18F)

Example 2

According to the method shown below, a compound represented by Formula (C) (in Formula (C), j represents 4.5 and k represents 4.5) was obtained. Hereinafter, the compound represented by Formula (C) is referred to as a compound (C).

A compound represented by Formula (8) was synthesized using ethylene glycol monovinyl ether and epichlorohydrin.

Then, the compound (C) was obtained by performing the same operation as in Example 1, except that 3.17 g of the compound represented by Formula (8) was used instead of the compound represented by Formula (7) in Example 1.

¹H-NMR and ¹⁹F-NMR measurements of the obtained compound (C) were conducted, and a structure was identified from the following results.

¹H-NMR (acetone-D₆): δ [ppm]=3.40 to 3.55 (4H), 3.65 to 3.95 (10H), 4.00 to 4.15 (8H), 6.35 to 6.55 (6H)

¹⁹F-NMR (acetone-D₆): δ [ppm]=−51.5 to −55.5 (9F), −78.5 (2F), −80.5 (2F), −88.5 to −91.0 (18F)

Example 3

According to the method shown below, a compound represented by Formula (D) (in Formula (D), m represents 4.5 and n represents 4.5) was obtained. Hereinafter, the compound represented by Formula (D) is referred to as a compound (D).

A compound represented by Formula (9) was synthesized using 3-buten-1-ol and epichlorohydrin.

Then, the compound (D) was obtained by performing the same operation as in Example 1, except that 2.82 g of the compound represented by Formula (9) was used instead of the compound represented by Formula (7) in Example 1.

¹H-NMR and ¹⁹F-NMR measurements of the obtained compound (D) were conducted, and a structure was identified from the following results.

¹H-NMR (acetone-D₆): δ [ppm]=1.90 to 2.05 (4H), 3.40 to 3.55 (4H), 3.65 to 3.85 (6H), 4.00 to 4.15 (8H), 5.10 to 5.15 (2H), 5.25 to 5.30 (2H), 5.85 to 5.95 (2H)

¹⁹F-NMR (acetone-D₆): δ [ppm]=−51.5 to −55.5 (9F), −78.5 (2F), −80.5 (2F), −88.5 to −91.0 (18F)

Example 4

According to the method shown below, a compound represented by Formula (F) (in Formula (F), r represents 4.5 and s represents 4.5) was obtained. Hereinafter, the compound represented by Formula (F) is referred to as a compound (F).

20 g of fluoropolyether (number average molecular weight of 1000 and molecular weight distribution of 1.1) represented by HOCH₂CF₂O(CF₂CF₂O)ᵣ(CF₂O)ₛCF₂CH₂OH (in the formula, r represents 4.5 and s represents 4.5) and 1.14 g of a compound represented by Formula (7), and 20 mL of t-butanol were put into a 200 mL eggplant flask under nitrogen atmosphere, and stirred at room temperature to be homogeneous.

0.90 g of potassium tert-butoxide was added to the homogeneous solution, and stirred at 70° C. for 8 hours to be reacted. The obtained reaction product was cooled to 25° C., neutralized with 1 mol/L of hydrochloric acid, and extracted with Vertrel XF manufactured by Du Pont-Mitsui Fluorochemicals Co., Ltd. (hereinafter, abbreviated as "Vertrel XF" in some cases), and washing was performed with water. An organic layer was dehydrated with anhydrous sodium sulfate and the desiccant was filtered off. Thereafter, a filtrate was concentrated. A residue was purified by silica gel column chromatography to obtain 5.68 g of a compound represented by Formula (17) in which an allyl group was bonded to one side of perfluoropolyether.

(In Formula (17), r represents 4.5 and s represents 4.5.)

A compound represented by Formula (11) was synthesized from glycerol α,α'-diallyl ether by oxidation using meta-chloroperbenzoic acid.

Then, 5.57 g of the compound represented by Formula (17), 1.13 g of the compound represented by Formula (11), and 50 mL of t-butanol were put into a 100 mL eggplant flask under nitrogen atmosphere, and stirred at room temperature to be homogeneous.

0.22 g of potassium tert-butoxide was added to the homogeneous solution, and stirred at 70° C. for 16 hours to be reacted. The obtained reaction product was cooled to 25° C., neutralized with 0.1 mol/L of hydrochloric acid, and extracted with Vertrel XF, and washing was performed with water. An organic layer was dehydrated with anhydrous sodium sulfate and the desiccant was filtered off. Thereafter, a filtrate was concentrated. A residue was purified by silica gel column chromatography to obtain the compound (F).

¹H-NMR and ¹⁹F-NMR measurements of the obtained compound (F) were conducted, and a structure was identified from the following results.

¹H-NMR (acetone-D₆): δ [ppm]=3.35 to 3.95 (15H), 3.95 to 4.15 (8H), 5.10 to 5.15 (2H), 5.25 to 5.30 (2H), 5.80 to 6.00 (2H)

¹⁹F-NMR (acetone-D₆): δ [ppm]=−51.5 to −55.5 (9F), −78.5 (2F), −80.5 (2F), −88.5 to −91.0 (18F)

Example 5

According to the method shown below, a compound represented by Formula (G) (in Formula (G), t represents 4.5 and u represents 4.5) was obtained. Hereinafter, the compound represented by Formula (G) is referred to as a compound (G).

Then, the compound (G) was obtained by performing the same operation as in Example 1, except that 4.14 g of the compound represented by Formula (11) was used instead of the compound represented by Formula (7) in Example 1.

¹H-NMR and ¹⁹F-NMR measurements of the obtained compound (G) were conducted, and a structure was identified from the following results.

¹H-NMR (acetone-D₆): δ [ppm]=3.35 to 3.65 (12H), 3.65 to 3.95 (8H), 3.95 to 4.02 (4H), 4.02 to 4.15 (4H), 5.05 to 5.20 (2H), 5.20 to 5.35 (2H), 5.80 to 6.00 (2H)

¹⁹F-NMR (acetone-D₆): δ [ppm]=−51.5 to −55.5 (9F), −78.5 (2F), −80.5 (2F), −88.5 to −91.0 (18F)

Example 6

According to the method shown below, a compound represented by Formula (H) (in Formula (H), v represents 4.5 and w represents 4.5) was obtained. Hereinafter, the compound represented by Formula (H) is referred to as a compound (H).

Then, the compound (H) was obtained by performing the same operation as in Example 4, except that 0.67 g of the compound represented by Formula (8) was used instead of the compound represented by Formula (11) in Example 4.

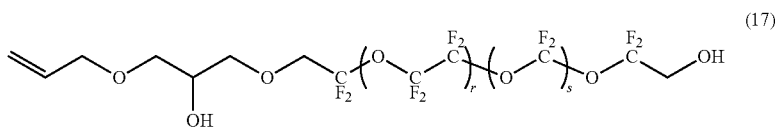

(17)

$^1$H-NMR and $^{19}$F-NMR measurements of the obtained compound (H) were conducted, and a structure was identified from the following results.

$^1$H-NMR (acetone-$D_6$): δ [ppm]=3.40 to 3.55 (4H), 3.65 to 3.95 (8H), 4.00 to 4.15 (8H), 5.10 to 5.15 (1H), 5.25 to 5.30 (1H), 5.85 to 5.95 (1H), 6.35 to 6.55 (3H)

$^{19}$F-NMR (acetone-$D_6$): δ [ppm]=−51.5 to −55.5 (9F), −78.5 (2F), −80.5 (2F), −88.5 to −91.0 (18F)

Example 7

According to the method shown below, a compound represented by Formula (I) (in Formula (1), x represents 4.5 and y represents 4.5) was obtained. Hereinafter, the compound represented by Formula (I) is referred to as a compound (I).

Then, the compound (I) was obtained by performing the same operation as in Example 1, except that 2.47 g of the compound represented by Formula (12) was used instead of the compound represented by Formula (7) in Example 1.

$^1$H-NMR and $^{19}$F-NMR measurements of the obtained compound (I) were conducted, and a structure was identified from the following results.

$^1$H-NMR (acetone-$D_6$): δ [ppm]=2.45 (2H), 3.45 to 3.60 (4H), 3.65 to 3.75 (2H), 3.75 to 3.80 (2H), 3.80 to 3.90 (2H), 4.00 to 4.15 (4H), 4.15 (4H)

$^{19}$F-NMR (acetone-$D_6$): δ [ppm]=−51.5 to −55.5 (9F), −78.5 (2F), −80.5 (2F), −88.5 to −91.0 (18F)

Example 8

According to the method shown below, a compound represented by Formula (J) (in Formula (J), z represents 4.5 and as represents 4.5) was obtained. Hereinafter, the compound represented by Formula (J) is referred to as a compound (J).

Then, the compound (J) was obtained by performing the same operation as in Example 4, except that 0.67 g of the compound represented by Formula (12) was used instead of the compound represented by Formula (11) in Example 4.

$^1$H-NMR and $^{19}$F-NMR measurements of the obtained compound (J) were conducted, and a structure was identified from the following results.

$^1$H-NMR (acetone-$D_6$): δ [ppm]=2.45 (1H), 3.45 to 3.60 (4H), 3.65 to 3.75 (2H), 3.75 to 3.95 (4H), 4.00 to 4.15 (6H), 4.15 (2H), 5.10 to 5.15 (1H), 5.25 to 5.30 (1H), 5.85 to 5.95 (1H)

$^{19}$F-NMR (acetone-$D_6$): δ [ppm]=−51.5 to −55.5 (9F), −78.5 (2F), −80.5 (2F), −88.5 to −91.0 (18F)

Example 9

According to the method shown below, a compound represented by Formula (K) (in Formula (K), ab represents 4.5 and ac represents 4.5) was obtained. Hereinafter, the compound represented by Formula (K) is referred to as a compound (K).

A compound represented by Formula (13) was synthesized using 3-butynyl-1-ol and epichlorohydrin.

Then, the compound (K) was obtained by performing the same operation as in Example 1, except that 3.40 g of the compound represented by Formula (13) was used instead of the compound represented by Formula (7) in Example 1.

$^1$H-NMR and $^{19}$F-NMR measurements of the obtained compound (K) were conducted, and a structure was identified from the following results.

$^1$H-NMR (acetone-$D_6$): δ [ppm]=2.10 (2H), 2.45 (4H), 3.40 to 3.55 (4H), 3.65 to 3.85 (6H), 4.00 to 4.15 (8H)

$^{19}$F-NMR (acetone-$D_6$): δ [ppm]=−51.5 to −55.5 (9F), −78.5 (2F), −80.5 (2F), −88.5 to −91.0 (18F)

Example 10

According to the method shown below, a compound represented by Formula (L) (in Formula (L), ad represents 4.5 and ae represents 4.5) was obtained. Hereinafter, the compound represented by Formula (L) is referred to as a compound (L).

A compound represented by Formula (14) was synthesized using 4-pentynyl-1-ol and epichlorohydrin.

Then, the compound (L) was obtained by performing the same operation as in Example 1, except that 3.40 g of the compound represented by Formula (14) was used instead of the compound represented by Formula (7) in Example 1.

$^1$H-NMR and $^{19}$F-NMR measurements of the obtained compound (L) were conducted, and a structure was identified from the following results.

$^1$H-NMR (acetone-$D_6$): δ [ppm]=1.80 (4H), 2.00 (2H), 2.30 (4H), 3.40 to 3.55 (4H), 3.65 to 3.85 (6H), 4.00 to 4.15 (8H)

$^{19}$F-NMR (acetone-$D_6$): δ [ppm]=−51.5 to −55.5 (9F), −78.5 (2F), −80.5 (2F), −88.5 to −91.0 (18F)

Example 11

According to the method shown below, a compound represented by Formula (M) (in Formula (M), af represents 4.5 and ag represents 4.5) was obtained. Hereinafter, the compound represented by Formula (M) is referred to as a compound (M).

A compound represented by Formula (18) was obtained by an addition reaction of 2-propyn-1-ol and allyl glycidyl ether.

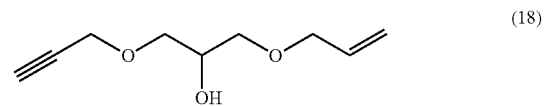

(18)

A compound represented by Formula (15) was synthesized from the compound represented by Formula (18) by oxidation using meta-chloroperbenzoic acid.

Then, the compound (M) was obtained by performing the same operation as in Example 1, except that 4.10 g of the compound represented by Formula (15) was used instead of the compound represented by Formula (7) in Example 4.

$^1$H-NMR and $^{19}$F-NMR measurements of the obtained compound (M) were conducted, and a structure was identified from the following results.

$^1$H-NMR (acetone-$D_6$): δ [ppm]=2.45 (2H), 3.35 to 3.65 (12H), 3.65 to 3.95 (8H), 3.95 to 4.15 (8H)

$^{19}$F-NMR (acetone-$D_6$): δ [ppm]=−51.5 to −55.5 (9F), −78.5 (2F), −80.5 (2F), −88.5 to −91.0 (18F)

Example 12

According to the method shown below, a compound represented by Formula (N) (in Formula (N), ah represents 4.5 and ai represents 4.5) was obtained. Hereinafter, the compound represented by Formula (N) is referred to as a compound (N).

A compound represented by Formula (19) in which an allyl group was bonded to one side of perfluoropolyether was obtained by performing the same operation as in Example 5, except that a using amount of the compound represented by Formula (11) in Example 5 was changed to 2.26 g.

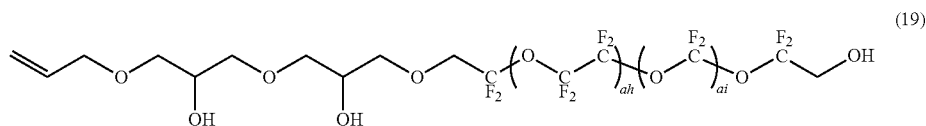
(19)

(In Formula (19), ah represents 4.5 and ai represents 4.5.)

Then, a compound represented by Formula (20) was obtained by an addition reaction of 4-pentynyl-1-ol and allyl glycidyl ether.

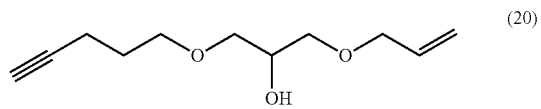
(20)

Further, a compound represented by Formula (16) was synthesized from the compound represented by Formula (20) by oxidation using meta-chloroperbenzoic acid.

Then, 5.00 g of the compound represented by Formula (19), 0.80 g of the compound represented by Formula (16), and 50 mL of t-butanol were put into a 200 mL eggplant flask under nitrogen atmosphere, and stirred at room temperature to be homogeneous.

0.15 g of potassium tert-butoxide was added to the homogeneous solution, and stirred at 70° C. for 18 hours to be reacted. The obtained reaction product was cooled to 25° C., neutralized with 0.1 mol/L of hydrochloric acid, and extracted with Vertrel XF, and washing was performed with water. An organic layer was dehydrated with anhydrous sodium sulfate and the desiccant was filtered off. Thereafter, a filtrate was concentrated. A residue was purified by silica gel column chromatography to obtain the compound (N).

$^1$H-NMR and $^{19}$F-NMR measurements of the obtained compound (N) were conducted, and a structure was identified from the following results.

$^1$H-NMR (acetone-$D_6$): δ [ppm]=1.80 (2H), 2.00 (1H), 2.30 (2H), 3.35 to 3.65 (12H), 3.65 to 3.95 (8H), 3.95 to 4.02 (4H), 4.02 to 4.15 (4H), 5.05 to 5.20 (1H), 5.20 to 5.35 (1H), 5.80 to 6.00 (1H)

$^{19}$F-NMR (acetone-$D_6$): δ [ppm]=−51.5 to −55.5 (9F), −78.5 (2F), −80.5 (2F), −88.5 to −91.0 (18F)

Example 13

According to the method shown below, a compound represented by Formula (O) (in Formula (O), aj represents 6.0) was obtained. Hereinafter, the compound represented by Formula (O) is referred to as a compound (O).

Then, the compound (O) was obtained by performing the same operation as in Example 1, except that 20 g of fluoropolyether represented by $HOCH_2CF_2CF_2O(CF_2CF_2CF_2O)_{aj}CF_2CF_2CH_2OH$ (number average molecular weight of 1000 and molecular weight distribution of 1.2) was used instead of the fluoropolyether in Example 1.

$^1$H-NMR and $^{19}$F-NMR measurements of the obtained compound (O) were conducted, and a structure was identified from the following results.

$^1$H-NMR (acetone-$D_6$): δ [ppm]=3.35 to 3.65 (12H), 3.65 to 3.95 (8H), 3.95 to 4.15 (8H), 5.05 to 5.20 (2H), 5.20 to 5.35 (2H), 5.80 to 6.00 (2H)

$^{19}$F-NMR (acetone-$D_6$): δ [ppm]=−130.00 to −129.00 (12F), −124.33 (4F), −86.42 (4F), −84.00 to −83.00 (24F)

Comparative Example 1

A compound represented by Formula (P) was synthesized by the method described in Patent document 1.

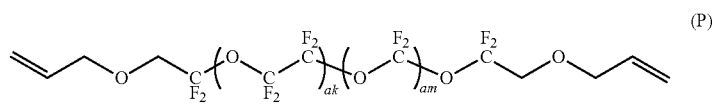
(P)

(In Formula (P), ak represents 4.5 and am represents 4.5.)

Comparative Example 2

A compound represented by Formula (Q) was synthesized by the method described in Patent document 3.

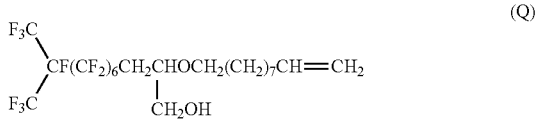

The number average molecular weights of the compounds of Examples 1 to 13 and Comparative Examples 1 and 2 obtained in these manners were determined by the $^1$H-NMR and $^{19}$F-NMR measurements described above. Results thereof are shown in Table 1.

TABLE 1

| | Compound | Number average molecular weight | Film thickness (Å) | Sliding time until coefficient of friction sharply increases (sec) | Si adsorption amount |
|---|---|---|---|---|---|
| Example 1 | (B) | 1225 | 8.5 | 938 | 0.48 |
| Example 2 | (C) | 1286 | 8.5 | 922 | 0.55 |
| Example 3 | (D) | 1254 | 9.0 | 941 | 0.52 |
| Example 4 | (F) | 1300 | 9.0 | 974 | 0.51 |
| Example 5 | (G) | 1374 | 9.5 | 927 | 0.40 |
| Example 6 | (H) | 1255 | 9.0 | 934 | 0.52 |
| Example 7 | (I) | 1221 | 9.0 | 945 | 0.54 |
| Example 8 | (J) | 1223 | 9.0 | 940 | 0.51 |
| Example 9 | (K) | 1249 | 9.0 | 933 | 0.50 |
| Example 10 | (L) | 1278 | 9.0 | 935 | 0.51 |
| Example 11 | (M) | 1370 | 9.0 | 943 | 0.44 |
| Example 12 | (N) | 1400 | 9.0 | 958 | 0.42 |
| Example 13 | (O) | 1621 | 9.5 | 970 | 0.39 |
| Comparative Example 1 | (P) | 1077 | 10.0 | 583 | 1.00 |
| Comparative Example 2 | (Q) | 682 | 10.0 | 438 | 1.15 |

Next, according to the method shown below, a lubricating layer forming solution was prepared using the compounds obtained in Examples 1 to 13 and Comparative Examples 1 and 2. Then, according to the method shown below, the lubricating layer of the magnetic recording medium was formed using the obtained lubricating layer forming solution, and magnetic recording media of Examples 1 to 13 and Comparative Examples 1 and 2 were obtained.

"Lubricating Layer Forming Solution"

Each of the compounds obtained in Examples 1 to 13 and Comparative Examples 1 and 2 was dissolved in Vertrel (registered trademark) XF (trade name, manufactured by Du Pont-Mitsui Fluorochemicals Co., Ltd.) as a fluorinated solvent, and was diluted with Vertrel, such that the film thickness when applied to the protective layer was 0.85 nm (8.5 Å) to 1.00 nm (10.0 Å), to form a lubricating layer forming solution.

"Magnetic Recording Medium"

A magnetic recording medium, in which an adhesion layer, a soft magnetic layer, a first base layer, a second base layer, a magnetic layer, and a protective layer were sequentially provided on a substrate having a diameter of 65 mm, was prepared. The protective layer was formed from carbon.

The lubricating layer forming solutions of Examples 1 to 13 and Comparative Examples 1 and 2 were applied by a dip method onto the protective layer of the magnetic recording medium in which each layer up to the protective layer was formed.

Thereafter, the magnetic recording medium to which the lubricating layer forming solution was applied was put into a thermostatic chamber at 120° C., and heat treatment was performed for 10 minutes. As a result, a lubricating layer was formed on the protective layer to obtain the magnetic recording medium.

A film thickness of lubricating layers of the obtained magnetic recording medium of Examples 1 to 13 and Comparative Examples 1 and 2 was measured using FT-IR (trade name: Nicolet iS50, manufactured by Thermo Fisher Scientific). Results thereof are shown in Table 1.

In addition, a wear resistance test and a chemical resistance test were conducted on the magnetic recording media of Examples 1 to 13 and Comparative Examples 1 and 2, according to the method shown below. Results thereof are shown in Table 1.

(Wear Resistance Test)

Using a pin-on-disk type friction and wear tester, an alumina ball having a diameter of 2 mm as a contact was slid on the lubricating layer of the magnetic recording medium, with a load of 40 gf at a sliding speed of 0.25 m/sec, to measure a coefficient of friction of a surface of the lubricating layer. Then, sliding time until coefficient of friction of the surface of the lubricating layer sharply increases was measured. The sliding time until the coefficient of friction sharply increases was measured four times for each lubricating layer of the magnetic recording medium, and an average value (time) thereof was used as an indicator of the wear resistance of the lubricant coating film.

The time until the coefficient of friction sharply increases can be used as an indicator of the wear resistance of the lubricating layer for the following reason. In the lubricating layer of the magnetic recording medium, wear progresses according to use of the magnetic recording medium. When the lubricating layer disappears due to the wear, the contact and the protective layer are in direct contact with each other to cause the coefficient of friction to sharply increase.

As shown in Table 1, the magnetic recording media of Examples 1 to 13 have a longer sliding time, until the coefficient of friction increases sharply, and were more favorable in wear resistance, compared to the magnetic recording media of Comparative Examples 1 and 2.

It is presumed that this is because in the magnetic recording media of Examples 1 to 13, in the fluorine-containing ether compound represented by Formula (1) which forms the lubricating layer, $R^1$ and $R^5$ each represents an alkenyl group having 2 to 8 carbon atoms or an alkynyl group having 3 to 8 carbon atoms, and $R^2$ and $R^4$ each represents a divalent linking group having a polar group.

(Chemical Resistance Test)

According to the evaluation method shown below, contamination of the magnetic recording medium was investigated by using an environmental substance that produces contaminant in a high temperature environment.

In the evaluation method shown below. Si ions were used as the environmental substance, and an Si adsorption amount was measured as the amount of the contaminant which was formed by the environmental substance and contaminated the magnetic recording medium.

Specifically, the magnetic recording medium to be evaluated was kept for 240 hours in the presence of siloxane Si rubber under a high temperature environment of a temperature of 85° C. and a humidity of 0%.

Next, the Si adsorption amount on the surface of the magnetic recording medium was analyzed and measured using secondary ion mass spectrometry (SIMS) to evaluate the degree of contamination due to the Si ions as the Si adsorption amount. In the evaluation of the Si adsorption amount, evaluation was performed by using a relative value when the result of Comparative Example 1 is 1.00. Results thereof are shown in Table 1.

As shown in Table 1, it became clear that the magnetic recording media of Examples 1 to 13 have a small Si adsorption amount and are less likely to be contaminated by the environmental substance under the high temperature environment, as compared to the magnetic recording media of Comparative Examples 1 and 2.

INDUSTRIAL APPLICABILITY

According to fluorine-containing ether compound of the present invention, a magnetic recording medium which is excellent in reliability of the magnetic recording medium, in particular, in the suppression of silicon contamination and the wear resistance, corresponds to low flying height of a magnetic head accompanying the rapid increase in recording density in recent years, and has high reliability even under a very severe environment associated with the diversification of applications, can be obtained.

In addition, the present invention provides a fluorine-containing ether compound which can be suitably used as a material for a lubricant for a magnetic recording medium which can realize excellent chemical resistance and wear resistance, even when the film thickness is reduced.

REFERENCE SIGNS LIST

- 10: Magnetic recording medium
- 11: Substrate
- 12: Adhesion layer
- 13: Soft magnetic layer
- 14: First base layer
- 15: Second base layer
- 16: Magnetic layer
- 17: Protective layer
- 18: Lubricating layer

The invention claimed is:

1. A fluorine-containing ether compound represented by Formula (1):

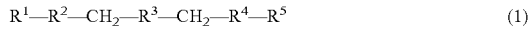

(in Formula (1), $R^1$ and $R^5$ may be the same as or different from each other and each represents an alkenyl group having 2 to 8 carbon atoms or an alkynyl group having 3 to 8 carbon atoms, $R^2$ and $R^4$ may be the same as or different from each other and each represents a divalent linking group having a polar group, and $R^3$ represents a perfluoropolyether chain, with a proviso that $R^1$ and $R^2$ are, and $R^4$ and $R^5$ are divided due to the presence of an atom other than the carbon atom such as an oxygen atom.).

2. The fluorine-containing ether compound according to claim 1,
wherein $R^1$ and $R^5$ each represents an alkenyl group having 2 to 5 carbon atoms or an alkynyl group having 3 to 5 carbon atoms.

3. The fluorine-containing ether compound according to claim 2,
wherein $R^1$ and $R^5$ each represents one selected from the group consisting of a vinyl group, an allyl group, a 3-butenyl group, a 4-pentenyl group, a propargyl group, a 3-butynyl group, and a 4-pentynyl group.

4. The fluorine-containing ether compound according to claim 1,
wherein the polar group included in $R^2$ and $R^4$ is a hydroxy group.

5. The fluorine-containing ether compound according to claim 1,
wherein $R^2$ and $R^4$ are represented by Formula (2-1) or (2-2)

(in Formula (2-1), a represents 1 to 3)

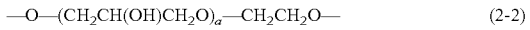

(in Formula (2-2), a represents 1 to 3).

6. The fluorine-containing ether compound according to claim 1,
wherein $R^3$ is represented by any one of Formulas (3) to (5)

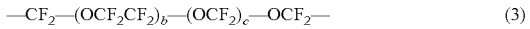

(in Formula (3), b and c each represents 0 to 20, but b and c are not 0 simultaneously)

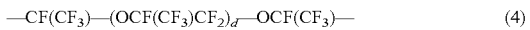

(in Formula (4), d represents 1 to 20)

(in Formula (5), e represents 1 to 20).

7. The fluorine-containing ether compound according to claim 1,
wherein a number average molecular weight thereof is within a range of 500 to 10000.

8. The fluorine-containing ether compound according to claim 1,
wherein the fluorine-containing ether compound is any one of compounds represented by Formulas (A) to (O)

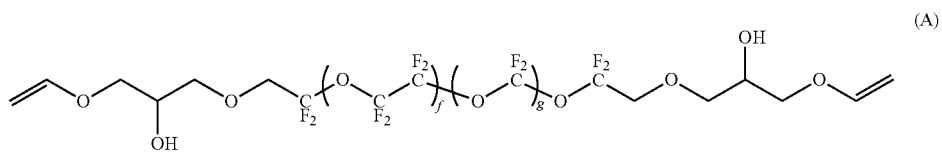

(in Formula (A), f and g each represents 0 to 7, and f and g are not 0 simultaneously)

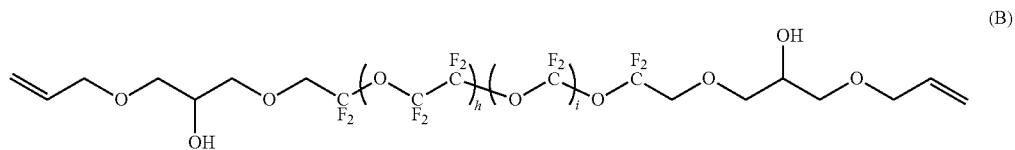
(B)

(in Formula (B), h and i each represents 0 to 7, and h and i are not 0 simultaneously)

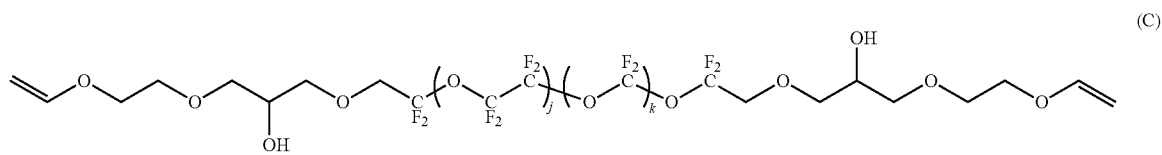
(C)

(in Formula (C), j and k each represents 0 to 7, and j and k are not 0 simultaneously)

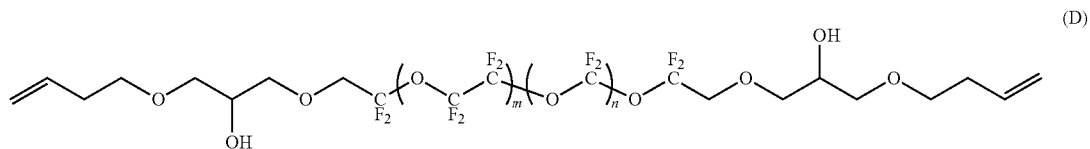
(D)

(in Formula (D), m and n each represents 0 to 7, and m and n are not 0 simultaneously)

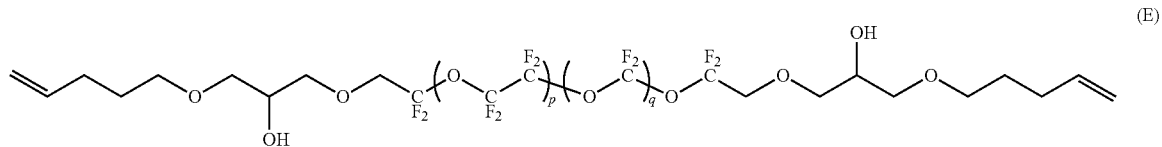
(E)

(in Formula (E), p and q each represents 0 to 7, and p and q are not 0 simultaneously)

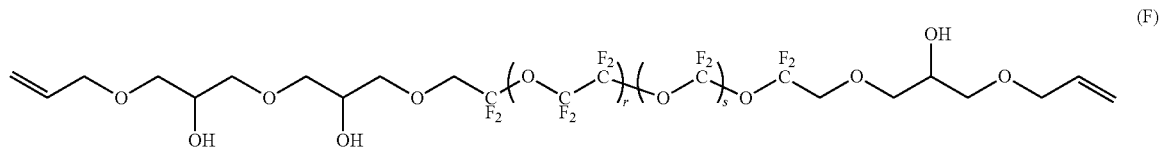
(F)

(in Formula (F), r and s each represents 0 to 7, and r and s are not 0 simultaneously)

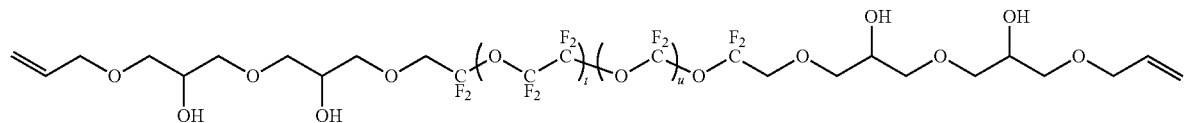

(G)

(in Formula (G), t and u each represents 0 to 7, and t and u are not 0 simultaneously)

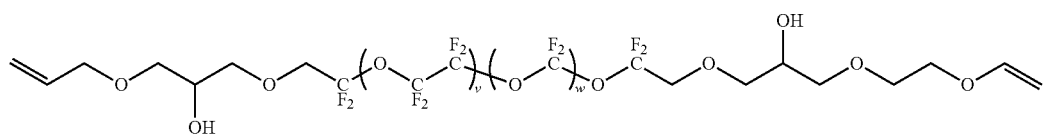

(H)

(in Formula (H), v and w each represents 0 to 7, and v and w are not 0 simultaneously)

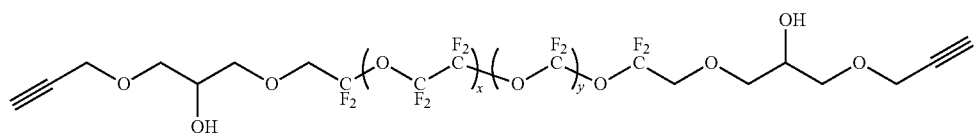

(I)

(in Formula (I), x and y each represents 0 to 7, and x and y are not 0 simultaneously)

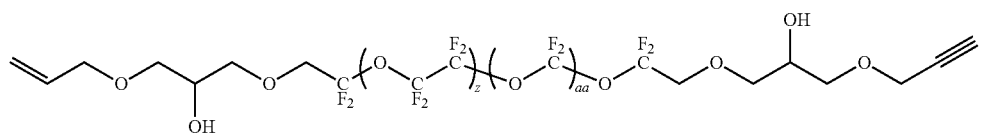

(J)

(in Formula (J), z and aa each represents 0 to 7, and z and aa are not 0 simultaneously)

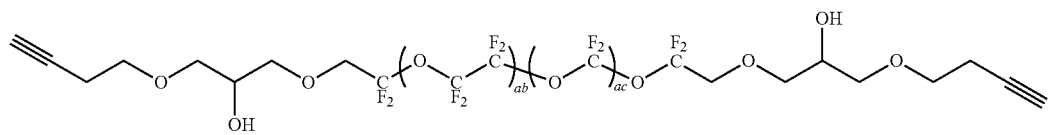

(K)

(in Formula (K), ab and ac each represents 0 to 7, and ab and ac are not 0 simultaneously)
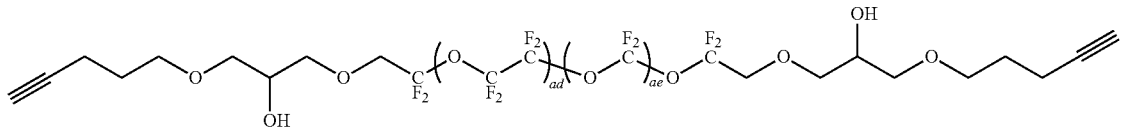
(L)
(in Formula (L), ad and ae each represents 0 to 7, and ad and ae are not 0 simultaneously)
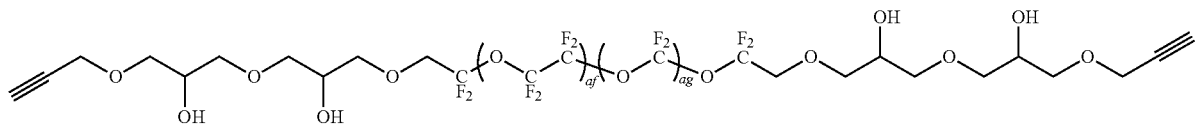
(M)
(in Formula (M), af and ag each represents 0 to 7, and af and ag are not 0 simultaneously)
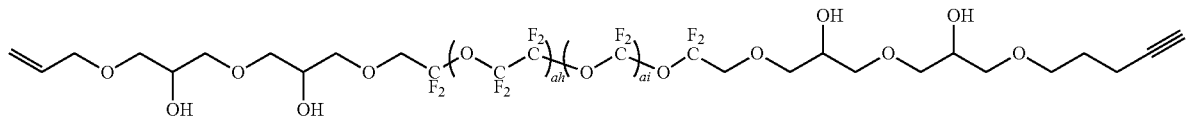
(N)
(in Formula (N), ah and ai each represents 0 to 7, and ah and ai are not 0 simultaneously)
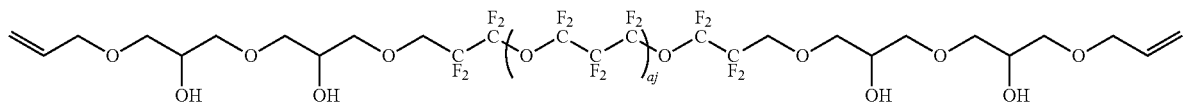
(O)
(in Formula (O), aj represents 1 to 7).
* * * * *